United States Patent [19]
Sussman et al.

[11] Patent Number: 5,632,982
[45] Date of Patent: May 27, 1997

[54] CYTOTOXIC ENHANCEMENT OF TNF WITH COPPER

[75] Inventors: Howard H. Sussman, Menlo Park; H. Garrett Wada, Atherton; Katherine S. Fok, Mountain View, all of Calif.

[73] Assignee: The Board of Trustees of the Leland Stanford Junior University, Palo Alto, Calif.

[21] Appl. No.: 255,265

[22] Filed: Jun. 7, 1994

[51] Int. Cl.$^6$ .................. A61K 38/19; A61K 33/34; A61K 39/00
[52] U.S. Cl. ............ 424/85.1; 424/604; 424/138.1; 424/143.1; 424/178.1; 424/179.1; 424/181.1
[58] Field of Search ............... 424/85.1, 604, 424/138.1, 143.1, 178.1, 179.1, 181.1

[56] References Cited

U.S. PATENT DOCUMENTS

| | | | |
|---|---|---|---|
| 4,863,727 | 9/1989 | Zimmerman et al. | 424/85.2 |
| 4,980,160 | 12/1990 | Goldberg et al. | 424/85.1 |
| 5,211,945 | 5/1993 | Wallach et al. | |

FOREIGN PATENT DOCUMENTS

WO91/16071 10/1991 WIPO.

OTHER PUBLICATIONS

"Platinum and Other Metal Coordination Compounds in Cancer Chemotherapy," Padua, Italy, Jun. 29–Jul. 2, 1987; Martinus Nijhoff Publishing.

"Structure, Magnetic Properties and Antineopoastic Activity of Novel Phthalato–Bridged Copper (II) Complexes," by C.A. Tsipis, et al., pp. 749–756.

"Antitumor Effect of a Copper Coordination Compounds with Superoxide Dismutase–Like Activity," by S. Leuthauser, et al., JNCI, vol. 66, No. 6, Jun. 1981, pp. 1077–1081.

"Enhancement of the Chromosome–damaging Action of Ascorbate by Transition Metals," by H.F. Stitch, et al., Cancer Research 39, 4145–4151, Oct., 1979.

"Glucose Depletion Enhances the Anti–Tumor Effect of TNF," by S. Volland, et al., Int. J. Cancer: 52, 384–390 (1992).

"Comparative In Vitro Studies of the Potentiation of Tumor Necrosis Factor (TNF)–α, TNF–β, and TNF–sam2 Cytotoxicity by Hyperthermia," by S.P. Tomasovic, et al., Journal of Immunotherapy, 11:85–92, 1992, Raven Press, Ltd., Ny.

"Antibody–Mediate Delivery of Tumor Necrosis Factor (TNF–α): Improvement of Cytotoxicity and Reduction of Cellular Resistance," by M.G. Rosenblum, et al., Cancer Communication, vol. 3, No. 1, 1991, pp. 21–27.

"Synergistic Cytotoxicity of Recombinant Human TNF and Various Anti–Cancer Drugs," by N. Watanabe, et al., Immunopharmacology & Immunotoxicology, 10(1), 117–127 (1988).

Pierson Cancer Treatment Report vol. 69 No. 11 1985 p. 1283.

*Primary Examiner*—Toni R. Scheiner
*Attorney, Agent, or Firm*—Bret E. Field; Fish & Richardson P.C.

[57] ABSTRACT

Copper chelates serve as cytotoxic agents in conjunction with a surface membrane protein receptor internalizing agent, particularly TNF, which has independent cytotoxic activity, for use against target cells. By employing concentrations of the two agents, where the agents have substantially reduced adverse side effects, the combination is shown to have effective cytotoxic activity.

12 Claims, No Drawings

CYTOTOXIC ENHANCEMENT OF TNF WITH COPPER

TECHNICAL FIELD

The field of this invention is anti-neoplastic activity.

BACKGROUND

Cancer has become an all-pervasive threat to a society with an ever-increasing elderly population. In addition to the numerous cancers which are genetically determined, cancers resulting from contacts with mutagens or other neoplastic-inducing agents, there is the additional factor that as the population ages, the likelihood of cells becoming cancerous appears to increase. Therefore, there has been ever-increasing efforts to find treatments which are capable of controlling tumor growth, reducing tumor burden and inhibiting metastasis. In view of the great diversity of types of cancers, the differing cellular mechanisms associated with a particular type of cancer, and the apparent differences in response of tumors to different agents, no one agent would appear to be satisfactory in the treatment of neoplasia. Because cancer cells are cells of the host whose phenotype has changed, resulting in uncontrolled growth and lack of differentiation, it has been very difficult to develop agents which can distinguish between normal host cells and the neoplastic cells.

The primary target has been cells which are rapidly proliferating. While this group of cells includes the neoplastic cells, it also includes leukocytes, which are essential to the immune system. However, in view of the morbidity associated with cancer, irradiation and chemotherapeutic approaches have been the primary therapeutic modality.

While for the most part the cytotoxic compounds have been synthetic organic compounds, there has also been interest in some naturally occurring compounds, which appear to have anti-tumor effect. One of these compounds is tumor necrosis factor ("TNF"), which includes TNF-$\alpha$ and -$\beta$. Where TNF is used, it is intended that either or both TNF-$\alpha$ and -$\beta$ are intended. While TNF is active against tumor cells, it also has a broad spectrum of other physiological activities, so as to have substantial side effects. However, the promise of using TNF has encouraged investigations in ways in which TNF may be employed, while reducing the level of side effects associated with a TNF-based therapy.

Relevant Literature

References describing the use of copper chelates in the treatment of cancer include: Morazzoni et al., "Platinum and other metal combination compounds in cancer chemotherapy," *Proceedings of the 5th International Symposium on Platinum and Other Metal Coordination Compounds in Cancer Chemotherapy*, Italy (Jun. 29–Jul. 2, 1987); Tsipis et al., "Structure, magnetic properties and anti-neoplastic activity of novel phthalato-bridged copper (II) complexes," supra; Pettit et al., *J. Inorg. Biochem.* 45: 230–1, 1992; Leuthauser et al., *J. Natl. Cancer Inst.* 66: 1077–81, Stich et al., *Cancer Res.* 39: 4145–51, 1979; Fok et al., Abstract No. 1068, ASCB Program, Dec. 1992, Molecular Biology of the Cell, Vol. 3, 186, 1992

References to the use of TNF-$\alpha$ for the treatment of neoplasia, particularly in combination with other agents includes Volland et al., *Int. J. Cancer* 52: 384–90, 1992 (glucose deprivation); Tomasovich et al., *J. Immunother.* 11: 85–92, 1992 (hypothermia); Rosenblum et al., *Cancer Commun.* 3: 21–7, 1991 (antibody-mediated delivery); Watanabe et al., *Immunopharmacol Immunotoxicol* 10: 117–27, 1988 (cytotoxic drugs); U.S. Pat. No. 4,863,727 (INF-$\beta$ and IL-2); U.S. Pat. No. 4,980,160 (non-steroidal anti-inflammatory agents); WO91/16071 (conjugate with gp120); CA 2,012,166 (interferon); U.S. Pat. No. 5,211,945 (IL-1).

SUMMARY OF THE INVENTION

Methods and compositions are provided for killing cells using an effective amount of copper ion, particularly cuprous ion, optionally in conjunction with an ancillary agent, to provide cytotoxicity. The methods employ copper ion in a biologically active form and, optionally, a second composition for intracellular transport of the copper ion in cytotoxic available form. Particularly, weakly chelated cupric ion is administered to a cell under conditions where cuprous ion is available at the cell surface and is transported into the cell, desirably by induced active internalization of a surface membrane receptor. Kits are provided for the treatment.

DESCRIPTION OF SPECIFIC EMBODIMENTS

Methods of killing cells, particularly neoplastic cells are provided, employing copper ions. Particularly, a source of cuprous ion is adminstered to the cells, particularly as cupric chelates or as cuprous ion, preferably in conjunction with induction of surface membrane protein internalization, where the cuprous ion is coordinate complexed to the surface membrane protein. Of particular interest is the use of an internalizing ligand which has independent cytotoxic activity. By using a combination therapy, each of the components may be used below an individual cytotoxic dosage, avoiding adverse side effects. When one or both of the drugs are administered locally at the site of the lesion, the two drugs may be at therapeutic dosage, usually below, for local administration, depending upon the aggressiveness of the therapy.

A wide variety of copper chelates or other cuprous source may be employed, where the chelates have redox activity and are physiologically acceptable. The chelates will be weak chelates, where the stability constant for the chelate will be below about $\log\beta_o 12$, particularly below about $\log\beta_o 11.5$, and usually at least about $\log\beta_o 3.0$. For the most part, copper chelates with oxygen or nitrogen-containing chelating agents will be employed, particularly oxygen-containing chelating agents. Agents which may find use include o-phenanthroline, phthalato, isophthalato and teraphthalato; 1-hydroxy-4-(glycyl-histidyl-lysine)-anthraquinone; 3,5-diisopropylsalicylate; salicylate; glycine; tartrate; oxalate; etc., while cupric o-phenanthroline has been reported as enhancing the cytotoxic effect of TNF-$\alpha$. The chelate will usually be with cupric ion and may involve a single copper ion or a plurality of copper ions, so that a single moleucle may include a number of chelated copper ions.

In order to afford the cuprous ion, the cupric chelate may be employed in conjunction with a sufficient amount of a physiologically acceptable reducing agent to ensure that at least substantially all of the cupric ion is reduced to the cuprous ion. The reducing agent and cupric chelate may be mixed prior to administration, at the time of administration, e.g. by mixing in a syringe or simultaneous infusion, or the reagents added consecutively, where desirably the cupric chelate will be added first and the reducing agent will be added last. Where the therapeutic composition is administered at the site for treatment, desirably the agents will be added together or the copper ion will be in the cuprous oxidation state.

Various physiologically acceptable reducing agents may be employed. Of particular interest are thiol compounds, such as cysteine, N-acetyl cysteine, β- mercaptoethanol, glutathione, etc. Other reducing agents which may find use include ascorbate, and the like. Depending on the nature of the reducing agent, the reducing agent may be used in stoichiometric amount or in large excess, usually not more than about 3-fold excess.

The TNF which is employed may be obtained from a natural source, which naturally produces TNF-α or -β, or may be produced recombinantly, where the expression may occur in either prokaryotic or eukaryotic cells, particularly *E. coli*. The sequence of the gene for TNF-α, both genomic and cDNA, have been reported (Pennka, et al, (1984) *Nature* 312: 721–729) and methods for expression of recombinant TNF-α have been reported (Fiers (1991) in: *Tumor Necrosis Factors: Structure, Functions and Mechanism of Action* (Aggawarl and Vilcek, eds) Marcell Dekker, N.Y.). The particular source of TNF is not essential to this invention, so long as the TNF has the requisite binding activity and is free of undesirable contaminants.

Instead of using TNF, one may use TNF analogs, which may or may not have TNF physiologic activity, but still retain binding activity for binding to the TNF receptor. These analogs are truncated analogs, where a sufficient portion of the naturally occurring TNF is retained for binding, while the TNF molecule has been truncated to modify its physiologic activity, one may use mutants, where one or more amino acids have been deleted, substituted, or combinations thereof, so that the resulting mutated TNF retains binding activity, or one may use synthetic molecules which bind to the TNF receptor, as agonists or antagonists. The only biological activity that is required is that binding results in the internalization of the TNF receptor, so as to carry copper ions into the cell. These molecules may be prepared and screened for binding to the TNF receptor in accordance with conventional ways, particularly using a labeled TNF, e.g. radioisotope labeled, for competition with the candidate compound. By measuring the amount of radioactivity retained by the TNF receptor in the presence of the candidate compound, the binding affinity of the candidate compound can be determined. Similarly, one can label the candidate compounds and combine them with viable cells having TNF receptors, and determine the amount of the candidate compound which is internalized, by measuring the intracellular radioactivity. The TNF analogs or substitutes may be covalently conjugated to moieties capable of coordinately complexing or chelating copper, usually cupric, so as to provide concurrently the internalization signal and the copper ion. Since cupric will be reduced to cuprous under the ambient conditions of the cell, the cytotoxic cuprous ion will be present intracellularly. By employing combinations of histidine, lysine, arginine, aspartate, glutamate and/or cysteine joined to a TNF binding compound, one can complex the copper ion for intracellular transport. TNF may be modified by adding codons to the N- or C-terminus of the gene encoding TNF or mutated analog thereof, which codons encode the indicated amino acids, so as to complex the copper to the TNF recceptor binding sequence. Alternatively, chelated copper may be used, where the chelating agent has a functional group, e.g. amino, carboxy, thiol, etc., for covalently bonding to the TNF receptor binding moiety. Linking can be directed so as not to interfere with the binding of the TNF receptor binding moiety, although intracellular activity of the TNF, may be reduced or destroyed.

The manner of administration of the TNF may be varied widely. The TNF may be administered systemically parenterally, intravascularly, intramuscularly, intravenously, subcutaneously, intralesionally, or the like. The TNF may be introduced as a physiologically acceptable formulation, encapsulated, as a depot formulated with collagen, fibrinogen, hyaluronic acid, biodegradable polymers, e.g. polyglycolides, or the like. There is an extensive literature describing various methods of administration of TNF (see, for example, Saks and Rosenblum, *Immunol. Scr.* 56: 567–87, 1992).

The TNF may be administered by itself or in combination with other agents in addition to the copper chelates, particularly where the other agents are formulated in combination with the TNF, and under a number of different modalities. Thus, the TNF may be introduced into vesicles, which include antibodies for directing the vesicle to a particular cancer site. The TNF may be administered under conditions of glucose deprivation or hyperthermia. The TNF may be conjugated to antibodies for directed application to the lesion. Other agents which may be used in combination with TNF include interferon-γ, IL-1, or the like. For the most part, the only other anti-cancer drug which will be employed in combination with TNF will be the copper chelate, although in specific situations other anti-cancer drugs may find application as such are described by Watanabe et al., supra.

Because of the great diversity of methods of administration, the variation in responsiveness of neoplastic or other cells to TNF, the use of other compounds as adjuncts, and the like, no particular dosage range can be provided. However, the mount of TNF employed will generally be not greater than about 90%, more usually not greater than about 80%, and preferably not greater than about 75% of the dosage that would have been employed in the absence of the copper compound. Usually, the dosage will be at least about 25%, more usually at least about 50% of the dosage employed in the absence of the copper compound. Dosages of TNF-α which have been found to be effective in clinical trials range from about 0.02–0.05 mg/m$^2$ 5 times per week, given intermittently. (Canadian Patent No. 2,012,166)

So far as the dosage of the copper compound, it will usually be not more than about 90%, usually not more than about 75%, of the cytotoxic dosage in the absence of other cytotoxic agents, and may be as low as 10% or less of the cytotoxic dosage in the absence of other agents. Generally the localized concentration will be in the range of 0.01 to 10 µM. To the extent that the level of internalization of the cuprous ion can be controlled, by using intralesional administration, liposome targeting, or the like, the amount of the copper reagent employed may be subject to further reduction.

As evidenced by in vitro studies, localized concentrations of 1 ng/ml of TNF and about 1–2 µM of the copper agent are shown to have greatly enhanced cytotoxic effect on neoplastic cells.

Many of the surface membrane proteins are internalized upon binding to their ligand. Therefore, the subject method allows for specificity of targets, where the target cells have a particular surface membrane protein subject to internalization, which is not generally available on other cells, so some degree of selectivity can be achieved. Surface membrane receptors which are internalized include the insulin receptor, glucose transporter, EGF receptor, LDL receptor, transferrin receptor, NGF receptor, Bp50 receptor (B cell activation protein), etc., where the last two receptors find analogy with the TGF receptor (Schall, et al., (1990) *Cell*, 61, 361–370; Ding et al., (1989) *J. Biol. Chem.* 264, 3924–3929; and Smith et at., (1991) *J. of Imm.* 144, 162–169)). By combining the ligand with a copper source, one can enhance the cytotoxicity of the copper ion by providing for a mechanism of intracellular presentation of the copper in cytotoxic form. The ligands may be used at a safe level for the host, but at a cytotoxic effective level in conjunction with the copper compound for the target cell.

Instead of ligands, other agents which provide for internalization of a surface membrane protein capable of chelating copper ion and presenting the copper ion intracellularly in a cytotoxic form may be employed. For example, antibodies may be used for binding to surface membrane proteins, where binding of the antibodies to the surface membrane protein results in internalization. In some instances the binding of the antibody will be sufficient for activation and internalization of the surface membrane receptor. In other instances, capping may be necessary, whereby an antibody is employed to cross-link the bound antibodies and cap the antibodies, resulting in internalization.

A wide variety of neoplasias may be treated in accordance with the subject methodology, including carcinomas, melanomas, sarcomas, leukemias and lymphomas. Particular types of cancers include lung cancers, such as small cell carcinoma, ovarian cancers, prostate cancers, breast cancers, hepatomas, skin cancers, brain cancers, and the like.

In addition to neoplasias, other therapeutic situations exist where there is an interest in reducing a target population. For example, in transplantation and autoimmune diseases, the reduction in the number of target T cells is of interest. A surface receptor which may find use is TCR, CD4, CDC8, etc. Other situations include targeting adiposal cells for cosmetic weight reduction.

In many situations there will be in vitro applications of the subject invention. For example, the subject methodology may be used to free a cellular compositon of neoplastic cells. For example, where tissue is taken from a host and the cells are to be expanded or where blood is taken from a host and the cells are to be expanded, it is frequently desirable that there be no neoplastic cells. This may be in screening compounds for the physiological effect on normal cells, where the expanded cellular population is to be returned to the host, and the like.

The active compounds can be formulated in a variety of ways, depending upon the method of administration, using a physiologically acceptable medium. For the most part, the media will include water, saline, phosphate buffered saline, ethanol, balanced salt solutions, DMSO solutions, etc. For depots, the active compositions may be formulated with collagen, fibrinogen, or other polymeric composition which will provide for slow release of the drugs. The concentration of the active ingredients may be varied widely, depending upon the desired dosage, manner of administration, solubility in the medium, and the like.

Kits may be provided, where appropriate amounts of the active ingredients are combined or provided in separate containers. The active ingredients may be formulated or the carriers for the active ingredients supplied in separate containers for mixing immediately prior to use. Mixing chambers may be provided, where syringes comprising the vehicles may be employed for uniformly dispersing the active ingredient in the vehicle. The kit will normally provide containers having single dosages, so that no further measurements need be made.

The following examples are offered by way of illustration and not by way of limitation.

EXPERIMENTAL

Materials and Methods
  Cells and Reagents
  CEM-SS (4) and CEM-C1Ca cells were obtained from Chris Simonson (GeneLabs Inc., Redwood City, Calif.) and cultured in RPMI 1640 with L-Glutamine (Gibco, Grand Island, N.Y.) supplemented with penicillin/streptomycin (Gibco) and 10% fetal bovine serum (Sigma). The cells were split 1:10 every third day. The CEM C1Ca cells were transfected with a neomycin resistance marker and selected with 100 µg/ml Geneticin (G418). Unless otherwise specified, all chemicals and reagents were from Sigma Chemical Co. (St. Louis, Mo.). TNF-α, anti-hTNF-α antibody, and anti-hIL-2 antibody were from Genzyme (Cambridge, Mass.), and cupric chloride and o-phenanthroline were from Aldrich (Milwaukee, Wis.). Anti-human TNFR1 receptor monoclonal antibody, #4E4, Anti-human TNFR2 receptor monoclonal antibody, #1H9, Anti-human GP120 monoclonal antibody, #5B6, were from Genentech Inc. (S. San Francisco, Calif.).

Measurement of Extracellular Acidification using the Cytosensor Microphysiometer The cells were harvested on the third day after passage by centrifugation, and the cell pellets were resuspended into Loading Medium at 0.6 to $1 \times 10^6$ cells/ml. Loading Medium is Low Buffering RPMI (Molecular Devices Corp., Menlo Park, Calif.) supplemented with 10 mM HEPES. One ml of cell suspension was loaded into sterile cell capsule cups (Molecular Devices Corp.), as previously described using a fibrin clot to immobilize the cells (Wada et al. (1993) *J. Cellul. Physiol.* 154: 129–138). The assembled capsule cups were loaded into Cytosensor® microphysiometer chambers, and Running Medium, Low Buffering RPMI supplemented with penicillin/streptomycin and 1 mg/ml HSA (endotoxin-free human serum albumin, Miles Labs., Elkhart, Ind.), was pumped through each chamber. TNF-α and the test materials were added to 30 ml of Running Medium and applied to the cells approximately half an hour after the chambers were loaded on the microphysiometer. When necessary DMSO was used as a vehicle for dissolving test materials and diluted to less than 0.1% in Running Medium. The basal cellular acidification rate (metabolic rate) measured by the instrument (Parce, et al. (1989) *Science* 246: 243–247) was normalized to 100% of basal rate prior to the addition of TNF or other test materials.

FACS Analysis

CEM-SS and C1Ca cells were analyzed for TNFR1 and TNRF2 using cell surface monoclonal antibody staining and FACS analysis. A single cell suspension was prepared for each line by washing twice in PBS/1% fetal bovine serum. Cells were adjusted to 107 cells/ml in PBS/1% fetal bovine serum. An 100 µl aliquot from each cell line was incubated with 1 µg of either monoclonal anti-TNFR1 (4E4), anti-TNFR2 (1H9), or an irrelevant antibody (anti-GP120, 5B6) for 30 minutes on ice. The cells were washed 3× in PBS/1% fetal bovine serum and incubated with fluorescein conjugated sheep (Fab')$_2$ fragment to mouse IgG (Cappel, West Chester, Pa.) for 30 minutes on ice. The cells were washed 3× in PBS/1% fetal bovine serum and analyzed on a FAC-Scan (Becton Dickinson, San Jose, Calif.).

Results

The Effects of TNF-α on CEM Cells were Detectable as Alterations in Acidification Rate The microphysiometer measures the rate of extracellular acidification, a function of the cell's metabolism. Over time, cells in the microphysiometer tend to show an early period of equilibration during which their acidification rates either rise or fall to a new steady state, depending upon the particular cell line. The present studies were conducted with CEM-SS cells which are resistant to TNF-α induced cytotoxicity, and with a subclone, CEM-C1Ca, transfected with the neomycin resistance marker and grown in G418 (50 µg/ml). CEM-SS cells were loaded into Cytosensor chambers as described in Materials and Methods and exposed, starting at 0 time, continuously to 1 ng/ml TNF-α or to media alone. Acidification rates were monitored for approximately 18 hr. CEM-C 1 Ca cells were loaded and exposed to 0, 0.01 ng/ml, 0.1 ng/ml and 1 ng/ml TNF for approximately 18 hr. The acidification rates were normalized to 100% prior to TNF exposure.

The untreated CEM-SS cells showed an initial steep decrease in rate lasting less than 30 minutes which was followed by an increase over the initial 2–4 hours to 125% of the initial base line, and then showed a steady rise to 175% by 18 hours. In contrast, when CEM-SS cells in the microphysiometer were treated with 1 ng/ml recombinant h-TNF-α, the acidification rate was mildly stimulated above the controls values for 1–2 hrs, but after 4 hours there was a steady reduction in rate of acidification. After 18 hrs of TNF exposure, the acidification rate had fallen from a peak value of 160% of the initial value to 120%. The untreated cells continued to have an increased acidification which was 175% of the initial rate at 18 hours.

The C1Ca subclone of the CEM-SS cell line, was shown to be very sensitive to TNF cytotoxicity. Exposure to TNF at 1 ng/ml resulted in a drop in the acidification to 12% of the initial rate within 18 hours, and a concentration as low as 0.01 ng/ml resulted in a drop to a value 60% of the initial rate at 18 hrs. In order to examine the specificity of decrease in acidification rate as being a measure of TNF cytotoxicity, the effects of anti-TNF-α neutralizing antibody were tested. Cells were exposed in the microphysiometer chamber to 1 ng/ml TNF, media alone, 1 ng/ml TNF plus anti-TNF antisera, and anti-TNF antisera alone. Cells were treated with TNF plus anti-IL-2 antisera as a control, with anti-IL2 antisera, media alone, and TNF. The acidification rates were normalized to 100% prior to TNF exposure. Using the C1Ca cells, the neutralizing rabbit antiserum was shown to block the TNF mediated decrease in acidification rate. A control antiserum, rabbit anti-hIL-2, had no effect on the acidification rate decrease.

Anti-TNFR1 Receptor Antibody Blocks the Cytotoxic Response of CEM Cells to TNF-α

In order to determine whether the TNF activated metabolic changes in CEM cells were mediated through TNF receptor interactions, the CEM-SS and the C1Ca subclone were incubated with monoclonal anti-TNF receptor antibodies, anti-human TNFR1 (p55) and anti-TNFR2 (p70) (Pennica et al. (1991) *Biochem.* 31: 1134–1141; Marsters, et al., (1992) *J. Biol. Chem.* 267: 5747–5740) and analyzed by flow cytometry. Both of these cell lines were found to express only the TNFR1 receptor on their surface. C1Ca cells were loaded in four microphysiometer chambers and two chambers were pre-treated with 1 µg/ml anti-TNFR1 for 15 min. The cells were then treated continuously with the same antibody plus 1 ng/ml TNF-α or plus media. The other two chambers were pre-treated with an isotype matched, IgG$_{1k}$, anti-GP120 antibody as a control at 1 µg/ml. The cells were then treated continuously with the same antibody plus 1 ng/ml TNF-α or media. CEM-SS cells were loaded in microphysiometer chambers and pre-treated with either anti-TNFR1 antibody or control antibody as described above. The cells were then treated continuously with 1 µg/ml anti-TNFR1 antibody plus 1 ng/ml TNF or plus media. The other two chambers were pre-treated with control antibody at 1 µg/ml, and the cells were then treated continuously with the same antibody plus 1 ng/ml TNF or plus media. The acidification rates were normalized to 100% prior to TNF exposure. Pre- treatment of the C1Ca cells with anti-TNFR1 antibody, 4E4, 15 minutes prior to and during exposure to TNF-α, substantially blocked the cytotoxic response to TNF, but an isotype matched control antibody (anti-GP120) did not. Anti-TNFR2 antibody also did not block the cytotoxic response to TNF. The metabolic changes in CEM-SS cells in response to TNF were also substantially blocked by anti-TNFR1 antibody.

The Effect of Reducing and Oxidizing Agents on TNF Mediated Cytotoxicity

Because the presence of reducing agents such as N-α cetyl cysteine (NAC) has been reported to inhibit the activating effects of TNF-α on HIV-1 replication in T cells (Roederer et al. (1990) *PNAS USA* 87: 4884–4888) and NFkB transcriptional activation factor (Schreck et al. (1991) *EMBO J.* 10: 2247–2258), we tested the effects of reducing agents and oxidizing agents on TNF cytotoxicity using CEM-SS cells and its subclone C1Ca cells. C1Ca cells were loaded into microphysiometer chambers and pre-treated with reducing agents prior to exposure to TNF-α. After pre-treatment for 15 min with 10 mM β-mercaptoethanol (BME), the cells were continuously exposed to 1 ng/ml TNF plus BME or media plus BME. Untreated cells were exposed to 1 ng/ml TNF or media alone as controls. After pre-treatment for 15 rain with 10 mM N-acetylcysteine (NAC) the cells were continuously exposed to 1 ng/ml TNF plus NAC or media plus NAC. Untreated cells were exposed to 1 ng/ml TNF or media alone as controls. The acidification rates were normalized to 100% prior to exposure of cells to reducing agents. The addition of 10 mM β-mercaptoethanol caused a small decrease in the cytotoxic effect of TNF on C1Ca cells. The addition of 10 mM N-acetylcysteine (NAC) did not produce a significant reduction in the cytotoxic effect of TNF. Each reducing agent increased the basal acidification rates of both C1Ca and CEM-SS cells. Oxidizing agents, cupric o-phenanthroline or hydrogen peroxide enhanced the TNF cytotoxicity. In particular, cupric o-phenanthroline at 1 µM, a sub-toxic concentration, significantly enhanced cell killing by TNF in the TNF resistant CEM-SS cells. When 1 µM ferric o-phenanthroline was tested, no synergy with TNF cytotoxicity was observed. The anti-oxidant, BHA, did not inhibit nor did it accelerate the copper enhanced TNF cytotoxicity (Table 1). Dramatic inhibition of the copper enhanced cell killing was achieved by the addition of the copper chelator, diethyldithiocarbamic acid (DDCA), demonstrating the importance of free or weakly chelated copper. Relevant to the mechanism of copper toxicity, it was observed that the combination of 1 µM copper and reducing agent, 10 mM NAG, was cytotoxic to the CEM-SS cells. In separate experiments, a color change from blue to red confirmed the reduction of Cu(II) to Cu(I) in the presence of 10 mM NAG and 10 µM cupric o-phenanthroline. The color change was reversible, changing back after about 30 minutes due to air oxidation of the copper. As shown in Table 2, either agent alone was not cytotoxic. BHA at 25 µM also did not inhibit copper/reducing agent cytotoxicity. It was also observed that the combination of 1 µM cupric o-phenanthroline and 2 mM hydrogen peroxide was highly cytotoxic to the cells (Table 1), and that this cytotoxicity was blocked by DDCA, a strong copper chelator.

TABLE 1

Effects of Transition Metals on CEM-SS Cells in Combination with TNF-α

| Test Substances | Concentration | Acidification Rate (% Control)* |
|---|---|---|
| TNF-α | 1 ng/ml | 84 |
| TNF-α + Cu++/o-ph. (COP) | 1 ng/ml, 1 µM | 29 |
| TNF-α + Fe+++/o-ph. | 1 ng/ml, 1 µM | 94 |
| TNF-α + COP + DDCA | 1 ng/ml, 1 µM, 1 mM | 90 |
| TNF-α + COP + BHA | 1 ng/ml, 1 µM, 25 µM | 27 |

*Acidification rate after 10 hrs of treatment with 1 ng/ml TNF-α + Test Substance relative to treatment with Test Substance alone (100%).

TABLE 2

Effects of Copper Plus NAC or H2O2 on CEM-SS Cells.

| Test Substances | Concentration | Acidification Rate (% control)* | | |
|---|---|---|---|---|
| | | 2 hr | 5 hr | 10 hr |
| Control | 0 | 100 | 100 | 100 |
| Cu++/o-ph. (COP) | 1 µM | 107 | 110 | 109 |
| NAC | 10 mM | 161 | 118 | 109 |
| DDCA | 1 mM | 127 | 109 | 77 |
| COP + NAC | 1 µM, 10 mM | 120 | 65 | 20 |
| COP + NAC + DDAC | 1 µM, 10 mM, 1 mM | 106 | 92 | 73 |
| COP + NAC + BHA | 1 µM, 1 mM, 25 µM | 54 | 24 | 12 |
| COP + H2O2 | 1 µM, 2 mM | 94 | 54 | 16 |
| COP + H2O2 + DDAC | 1 µM, 2 mM, 1 mM | 117 | 135 | 131 |

*Acidification Rate at the specified time after continuous exposure to the various treatments was normalized to % of control, no treatment (100%).

The Copper Potentiated TNF Cytotoxicity is Inhibited by TNFR1 Antibody and TNFR1 Aggregation Triggers TNF Independent Copper Cytotoxicity The copper potentiated TNF cytotoxicity was inhibited by an anti-TNFR1 antibody known to be a TNF-α antagonist (Pennica et al., 1991 supra; Marsters, et al., 1992, supra). CEM-SS cells were loaded into microphysiometer chambers and monitored for acidification rate changes during their treatment with TNF in the presence and absence of COP. Cells were exposed to 1 ng/ml TNF, media alone, 1 µM COP, and 1 ng/ml TNF plus 1 µM COP. The acidification rates were normalized to 100% prior treatment with TNF and COP. CEM-SS cells were loaded into Cytosensor chambers and pre-treated with 1 µg/ml anti-TNFR1 antibody for 30 min prior to exposure to a combination of 1 µM cupric o-phenanthroline (COP) and 1 ng/ml TNF-α plus anti-TNFR1 or 1 µM COP plus anti-TNFR1. Cells were exposed to control isotype matched antibody (anti-GP120) for 30 rain prior to exposure to 1 µM COP plus anti-GP120 as controls. CEM-SS cells were tested for their response to capping of the TNFR1 receptors in the presence of COP. After pre-treatment for 15 rain with 1 µg/ml anti-TNFR1, cells were exposed to anti-mouse IgG for 15 rain and then continuously exposed to 1 µM COP alone. Control treatments were run which consisted of pre-treatment with anti-TNFR1 antibody, no anti-IgG treatment, and continuously exposed to COP; no pretreatment with anti-TNFR1 antibody, pre-treatment with anti-IgG and continuously exposed to COP; and no pre-treatment and continuously exposed to COP. Acidification rates were normalized to 100% prior to the time of antibody exposure. When CEM-SS cells were pre-treated for 15 minutes with the anti-R1 antibody, the copper potentiated killing was reduced approximately 50%. It was also noted that when cells were treated with anti-R1 and copper alone, the cells exhibited a slowly developing decrease in metabolic activity which suggested that low level activation of the receptor may be occurring. In order to determine whether antibody mediated aggregation of the TNFR1 receptors could also trigger the copper potentiated cytotoxic response, anti-mouse IgG antibody was used following anti-R1 to cause receptor capping. The second antibody treatment triggered the copper potentiated cytoxic response in the absence of TNF to the same extent as 1 ng/ml TNF.

Quinacrine Inhibits the TNF Activated Metabolic Changes in CEM Cells, but not the Copper Potentiated Cell Killing When CEM-SS cells were pre-treated for 30 minutes with 10 µM quinacrine, a phospholipase A2 inhibitor, and then exposed to a moderate level (0.1 ng/ml) of TNF, the expected metabolic alterations which are observed with control cells were inhibited. When this same experiment is done in the presence of 1 µM cupric o-phenanthroline, we observed no significant inhibition of the copper potentiated TNF cytotoxicity. Quinacrine was tested for its effect on TNF cytotoxicity. CEM-SS cells were loaded in chambers and pre-treated for 30 rain with 10 µM quinacrine and then exposed to 0.1 ng/ml TNF-α plus quinacrine for 18 hrs or media plus quinacrine (open squares). Control cells were mock pre-treated with media alone and exposed to 0.1 ng/ml TNF-α for 18 hrs or media. CEM-SS cells were treated as above with the addition of 1 µM COP to the media at the time of TNF exposure. Cells were pre-treated for 30 min with 10 µM quinacrine and then exposed to 0.1 ng/ml TNF-α and 1 µM COP plus quinacrine for 18 hrs or media plus 1 µM COP and quinacrine. Control cells were mock pre-treated with media alone and exposed to 0.1 ng/ml TNF-α and 1 µM COP for 18 hrs or media plus 1 µM COP. Acidification rates were normalized to 100% prior to the time of TNF exposure.

It is evident from the above results, that the presence of copper can greatly enhance the cytotoxicity of TNF. The above results show that while TNF can have some cytotoxic effect on resistant transformed leukemia cells, the cytotoxic effect is greatly enhanced in the presence of a copper chelate at a concentration which does not otherwise differ significantly from a control medium. By employing a combination of a copper chelate, which is shown to have little or no cytotoxic effect with TNF at a level where the TNF has only low cytotoxic effect, one can substantially avoid the adverse side effects associated with TNF treatment of neoplasia.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for killing target cells, said method comprising:
  combining said target cells with a source of cuprous ion in a form capable of binding to a surface membrane protein receptor, said source being other than cupric o-phenanthroline in the absence of a reducing agent, and an agent which binds to said surface membrane protein receptor and induces the internalization of said surface membrane protein receptor in an amount to provide a cytotoxic amount of cuprous ion internalized within said cells, wherein each component is administered in an amount below its individual cytotoxic amount;

whereby said target cells are killed.

2. A method according to claim 1, wherein said source of cuprous ion comprises cupric ion in combination with a physiologically acceptable reducing agent.

3. A method according to claim 1, wherein said agent is a ligand for said surface membrane protein receptor.

4. A method according to claim 3, wherein said agent is present below a cytotoxic concentration in the absence of said source of cuprous ion.

5. A method according to claim 4, wherein said agent is TNF.

6. A method according to claim 1, wherein said target cells are neoplastic cells.

7. A method according to claim 1, wherein said target cells are lymphocytes or adipocytes.

8. A method according to claim 1, wherein said agent is a combination of surface membrane protein receptor binding antibodies and anti-antibodies.

9. A method for killing target neoplastic cells, said method comprising:

combining said target cells with a mixture of a weak cupric chelate and a cupric reducing agent to provide a source of cuprous ion and an agent which binds to a surface membrane protein receptor of said target cells and induces the internalization of said surface membrane protein receptor, said mixture of weak cupric chelate and cupric reducing agent in an amount to provide a cytotoxic amount of cuprous ion internalized within said cells, wherein each component is administered in an amount below its individual cytotoxic amount;

whereby said target cells are killed.

10. A method according to claim 9, wherein said cupric chelate is cupric o-phenanthroline below a cytotoxic concentration in the absence of a reducing agent.

11. A method according to claim 9, wherein said agent is TNF at a concentration below a cytotoxic concentration of TNF in the absence of cuprous ion.

12. A method according to claim 9, wherein said agent is a combination of surface membrane protein receptor binding antibodies and anti-antibodies.

* * * * *

UNITED STATES PATENT AND TRADEMARK OFFICE
CERTIFICATE OF CORRECTION

PATENT NO. : 5,632,982
DATED : May 27, 1997
INVENTOR(S) : Sussman, Wada and Fok

It is certified that error appears in the above-identified patent and that said Letters Patent is hereby corrected as shown below:

Title page, [73], Assignee, the 3rd line, after "Calif.", insert --; Molecular Devices Corporation, Sunnyvale, Calif.--.

| | |
|---|---|
| Column 8, line 55 | "NAG" should read --NAC-- |
| Column 8, line 58 | "NAG" should read --NAC-- |
| Column 9, line 60 | "rain" should read --min-- |
| Column 9, line 61 | "rain" should read --min-- |
| Column 10, line 26 | "rain" should read --min-- |

Signed and Sealed this

Sixth Day of July, 1999

Attest:

Q. TODD DICKINSON

*Attesting Officer*     *Acting Commissioner of Patents and Trademarks*